US007579012B2

(12) United States Patent
Kolattukudy et al.

(10) Patent No.: US 7,579,012 B2
(45) Date of Patent: Aug. 25, 2009

(54) TARGETING OF TRIACYLGLYCEROL SYNTHASE GENE FOR TUBERCULOSIS TREATMENT

(75) Inventors: Pappachan E. Kolattukudy, Orlando, FL (US); Tatiano Sirakova, Orlando, FL (US); Vinod S. Dubey, Waukegan, IL (US); Jaiyanth Daniel, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 19 days.

(21) Appl. No.: 11/561,477

(22) Filed: Nov. 20, 2006

(65) Prior Publication Data

US 2008/0014206 A1 Jan. 17, 2008

Related U.S. Application Data

(60) Provisional application No. 60/748,283, filed on Dec. 7, 2005.

(51) Int. Cl.

| | |
|---|---|
| *A61K 39/04* | (2006.01) |
| *A61K 39/02* | (2006.01) |
| *C07H 21/04* | (2006.01) |
| *C07H 21/02* | (2006.01) |

(52) U.S. Cl. .................... 424/248.1; 530/300; 530/350; 536/23.1; 536/23.7; 424/9.1; 424/9.2; 424/130.1; 424/139.1; 424/150.1; 424/184.1; 424/185.1; 424/190.1; 424/234.1

(58) Field of Classification Search .................. 424/9.1, 424/9.2, 130.1, 139.1, 150.1, 184.1, 185.1, 424/190.1, 234.1, 248.1; 530/300, 350; 536/23.1, 536/23.7

See application file for complete search history.

(56) References Cited

OTHER PUBLICATIONS

Daniel, J., et al. Induction of a novel class of diacylglycerol acyltransferasces and triacylglycerol accumulation in Mycobacterium tuberculosis as it goes into a dormancy-like state in culture. Journal of Bacteriology, vol. 186, No. 15, pp. 5017-5030, Aug. 2004.*

* cited by examiner

*Primary Examiner*—Rodney P. Swartz
(74) *Attorney, Agent, or Firm*—Timothy H. Van Dyke; Beusse Wolter Sanks Mora & Maire

(57) ABSTRACT

Disclosed herein are novel methods for screening for compounds useful in treating or preventing tuberculosis. In exemplary embodiments, screening methods are based on the implementation or manipulation of triacylglycerol synthase like polypeptides or polynucleotides encoding the same. The methods are useful in identifying agents active against TB infection.

17 Claims, 7 Drawing Sheets

A

B

A

B

A

B

C

SEQUENCE LISTING

<160> NUMBER OF SEQ ID NOS: 17

<210> SEQ ID NO 1
<211> LENGTH: 1392
<212> TYPE: DNA
<213> ORGANISM: Mycobacterium tuberculosis

<400> SEQUENCE: 1
atgaatcacc taacgacact tgacgccggg tttctcaagg cagaagacgt ggatcggcac 60
gtgagtctgg caatcggcgc tctggcggtc atcgaggggc cggctcccga tcaggaagcc 120
ttcttatcgt cgctcgctca acgcctacgt ccctgtaccc ggttcgggca gcggttacgc 180
ctgcgcccgt tcgacctcgg tgcacccaaa tgggtggacg atcccgactt cgatcttggc 240
cgtcatgtgt ggcgcatcgc cttgccgcgg cctggcaacg aagaccagtt attcgagctg 300
atcgccgatc tgatggcgcg tcgtttggac cggggtcgac cgctgtggga ggtctgggtc 360
atcgaaggcc tggcggacag caagtgggcg atcctgacca aactgcacca ctgcatggcc 420
gacggaatcg cggcgactca cctgctagct gggctctccg atgaaagtat gagcgacagc 480
ttcgcgagca acatccacac gaccatgcag tcgcaatccg catctgtgcg gcggggtgga 540
ttccgtgtca atccaagcga ggcgttgacc gcgtcgaccg ccgtgatggc aggcatcgtt 600
cgcgcggcca agggtgccag tgagatcgcg gccggcgtgc taagtcccgc cgcgtcgtcg 660
ttgaacgggc cgatcagtga tttgcgtcgc tacagcgcag caaaggtccc tctcgccgac 720
gtcgaacagg tgtgccggaa attcgacgtc accatcaatg atgttgcgct tgccgcgatt 780
acggaaagct accgcaacgt cctcatccag cggggtgagc ggcctaggtt tgattcgctg 840
cgtacgctag tgccggtctc gacgcgttcc aacagcgctt tgagcaagac cgataaccgt 900

-continued

```
gtttcgttaa tgctgcccaa cctgccggtg gatcaagaga acccgctgca gcggctgcgg    960
atcgtgcact cgcggctgac tcgggccaag gcgggggggac agagacaatt cggaaatact   1020
ttgatggcga ttgccaaccg ccttccgttc cccatgaccg catgggcggt cgggctgttg   1080
atgcggctgc cgcagcgtgg tgttgtcacc gtggcgacaa atgtgccggg tccacgacgg   1140
ccgctgcaga ttatgggcag acgggtgctt gacctatacc cggtttcgcc gatcgcgatg   1200
caactgcgca ccagtgtcgc gatgctcagc tacgccgacg acctgtactt cgggatcctg   1260
gccgactacg acgtggtagc agatgccggc cagctggcgc gaggaattga agacgccgtc   1320
gcacggctgg tggcgatcag taagcggcgc aaggtgactc gcaggcgcgg agcgctatcg   1380
ctggttgtgt ga                                                        1392
```

<210> SEQ ID NO 2
<211> LENGTH: 463
<212> TYPE: PRT
<213> ORGANISM: Mycobacterium tuberculosis

<400> SEQUENCE: 2

```
Met Asn His Leu Thr Thr Leu Asp Ala Gly Phe Leu Lys Ala Glu Asp
  1               5                  10                  15

Val Asp Arg His Val Ser Leu Ala Ile Gly Ala Leu Ala Val Ile Glu
                 20                  25                  30

Gly Pro Ala Pro Asp Gln Glu Ala Phe Leu Ser Ser Leu Ala Gln Arg
             35                  40                  45

Leu Arg Pro Cys Thr Arg Phe Gly Gln Arg Leu Arg Leu Arg Pro Phe
         50                  55                  60

Asp Leu Gly Ala Pro Lys Trp Val Asp Pro Asp Phe Asp Leu Gly
 65                  70                  75                  80

Arg His Val Trp Arg Ile Ala Leu Pro Arg Pro Gly Asn Glu Asp Gln
                 85                  90                  95

Leu Phe Glu Leu Ile Ala Asp Leu Met Ala Arg Arg Leu Asp Arg Gly
            100                 105                 110

Arg Pro Leu Trp Glu Val Trp Val Ile Glu Gly Leu Ala Asp Ser Lys
        115                 120                 125

Trp Ala Ile Leu Thr Lys Leu His His Cys Met Ala Asp Gly Ile Ala
130                 135                 140

Ala Thr His Leu Leu Ala Gly Leu Ser Asp Glu Ser Met Ser Asp Ser
145                 150                 155                 160

Phe Ala Ser Asn Ile His Thr Thr Met Gln Ser Gln Ser Ala Ser Val
                165                 170                 175

Arg Arg Gly Gly Phe Arg Val Asn Pro Ser Glu Ala Leu Thr Ala Ser
            180                 185                 190

Thr Ala Val Met Ala Gly Ile Val Arg Ala Lys Gly Ala Ser Glu
        195                 200                 205

Ile Ala Ala Gly Val Leu Ser Pro Ala Ala Ser Ser Leu Asn Gly Pro
    210                 215                 220

Ile Ser Asp Leu Arg Arg Tyr Ser Ala Ala Lys Val Pro Leu Ala Asp
225                 230                 235                 240

Val Glu Gln Val Cys Arg Lys Phe Asp Val Thr Ile Asn Asp Val Ala
                245                 250                 255

Leu Ala Ala Ile Thr Glu Ser Tyr Arg Asn Val Leu Ile Gln Arg Gly
            260                 265                 270

Glu Arg Pro Arg Phe Asp Ser Leu Arg Thr Leu Val Pro Val Ser Thr
        275                 280                 285
```

```
Arg Ser Asn Ser Ala Leu Ser Lys Thr Asp Asn Arg Val Ser Leu Met
    290                 295                 300

Leu Pro Asn Leu Pro Val Asp Gln Glu Asn Pro Leu Gln Arg Leu Arg
305                 310                 315                 320

Ile Val His Ser Arg Leu Thr Arg Ala Lys Ala Gly Gly Gln Arg Gln
                325                 330                 335

Phe Gly Asn Thr Leu Met Ala Ile Ala Asn Arg Leu Pro Phe Pro Met
                340                 345                 350

Thr Ala Trp Ala Val Gly Leu Leu Met Arg Leu Pro Gln Arg Gly Val
            355                 360                 365

Val Thr Val Ala Thr Asn Val Pro Gly Pro Arg Arg Pro Leu Gln Ile
    370                 375                 380

Met Gly Arg Arg Val Leu Asp Leu Tyr Pro Val Ser Pro Ile Ala Met
385                 390                 395                 400

Gln Leu Arg Thr Ser Val Ala Met Leu Ser Tyr Ala Asp Asp Leu Tyr
                405                 410                 415

Phe Gly Ile Leu Ala Asp Tyr Asp Val Val Ala Asp Ala Gly Gln Leu
                420                 425                 430

Ala Arg Gly Ile Glu Asp Ala Val Ala Arg Leu Val Ala Ile Ser Lys
            435                 440                 445

Arg Arg Lys Val Thr Arg Arg Gly Ala Leu Ser Leu Val Val
    450                 455                 460

<210> SEQ ID NO 3
<211> LENGTH: 110
<212> TYPE: PRT
<213> ORGANISM: Mycobacterium tuberculosis

<400> SEQUENCE: 3

Met Val Gln Gly Arg Thr Val Leu Phe Arg Thr Ala Glu Gly Ala Lys
1               5                   10                  15

Leu Phe Ser Ala Val Ala Lys Cys Ala Val Ala Phe Glu Ala Asp Asp
            20                  25                  30

His Asn Val Ala Glu Gly Trp Ser Val Ile Val Lys Val Arg Ala Gln
        35                  40                  45

Val Leu Thr Thr Asp Ala Gly Val Arg Glu Ala Glu Arg Ala Gln Leu
    50                  55                  60

Leu Pro Trp Thr Ala Thr Leu Lys Arg His Cys Val Arg Val Ile Pro
65                  70                  75                  80

Trp Glu Ile Thr Gly Arg His Phe Arg Phe Gly Pro Glu Pro Asp Arg
                85                  90                  95

Ser Gln Thr Phe Ala Cys Glu Ala Ser Ser His Asn Gln Arg
            100                 105                 110

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcatgatctt ggcgatctcc agc                                           23

<210> SEQ ID NO 5
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctgcagggtg attcatggtc agc                                              23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctcgagacgt ggtagcagat gcc                                              23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcatgatact tcccgcactg ccc                                              23

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttatcgtcgc tcgctcaacg cc                                               22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tttccgtaat cgcggcaagc gc                                               22

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cggcattgat cggtgcccaa ccc                                              23

<210> SEQ ID NO 11
<211> LENGTH: 24
<212> TYPE: DNA
```

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
tgaggcgatg gtggtgtcga tgct                                      24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
ggaactggcg cagttcctct gggg                                      24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
tcacgcccaa actccaacac accg                                      24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
tgggtcgtcg acatgggtgg cgag                                      24

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
cgtgctaagt cccgccgcgt c                                         21

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gtggcgtgtt ctggacccga agcg                                      24

<210> SEQ ID NO 17
<211> LENGTH: 24
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 17
gtccatcgac tacgcctgtc ggcc                                              24
```

TARGETING OF TRIACYLGLYCEROL SYNTHASE GENE FOR TUBERCULOSIS TREATMENT

CROSS-REFERENCE TO RELATED APPLICATIONS

This application is related to U.S. Provisional Patent No. 60/748,283 filed Dec. 7, 2005, which is incorporated herein by reference. Priority is claimed under 35 USC § 119.

GOVERNMENT SUPPORT

This invention was made through support from the NIH, Grant Nos. AI46582 and AI35272. The government may have certain rights in this invention.

BACKGROUND

Tuberculosis (TB) has been a major health problem for most of recorded history and *Mycobacterium tuberculosis* remains one of the world's most significant pathogens. Responsible for millions of new cases of tuberculosis annually (see e.g. Pablo-Mendez et al., (1998) New Engl. J. Med. 338, 1641-1649), it is the leading cause of death from a single infectious agent. While the incidence of the disease declined in parallel with advancing standards of living since at least the mid-nineteenth century, in spite of the efforts of numerous health organizations worldwide, the eradication of tuberculosis has never been achieved, nor is imminent.

TB is acquired by the respiratory route; actively infected individuals spread this infection efficiently by coughing or sneezing "droplet nuclei" which contain viable bacilli. Overcrowded living conditions and shared air spaces are especially conducive to the spread of TB, underlying the increase in instances that have been observed in the U.S. in prison inmates and among the homeless in larger cities.

Medical experts estimate that about 10 million Americans are infected with TB bacteria, and about 10 percent of these people will develop active TB in their lifetime. However, TB is an increasing worldwide problem, especially in Africa. It is estimated that, worldwide, about one billion people will become newly infected, over 150 million people will contract active TB, and 36 million people will die between now and 2020 unless TB control is improved.

The emergence of multi-drug resistant strains of *Mycobacterium tuberculosis* poses serious threats to the control of this disease due to the complex nature of second-line drug treatment (WHO Report. (2004) *WHO/HTM/TB/2004.343*). Upon infection the bacterium goes through an initial replicative phase inside the alveolar macrophages after which it enters a non-replicative, drug-resistant state of dormancy. This state of dormancy is probably induced by the environmental stress exerted upon the pathogen by the host's immune response. The bacterium is able to survive in this dormant state for decades until the host's immune system is weakened when it reactivates and causes the infectious disease (Dannenberg, Jr., A. M., and Rook G. A. W. (1994) In *Tuberculosis: Pathogenesis, Protection and Control*, Bloom, B. R., (Ed.) American Society of Microbiology, Washington D.C.). The current anti-mycobacterial drugs are able to kill only the actively replicating mycobacteria and do not clear the latent bacteria from the host (Honer zu Bentrup, K., and Russell D. G. (2001) *Trends Microbiol* 9, 597-605). Thus latency is a major problem in TB control. One-third of the world population is infected with the latent microorganism and nearly two million deaths occur annually (Dye, C., Scheele, S., Dolin, P., Pathania, V., and Raviglione M. C. (1999) *JAMA*. 282, 677-686, WHO Report. (2005) *WHO/HTM/TB/2005*). Individuals carrying a latent infection are estimated to harbor a 2-23% lifetime risk of reactivation (Zahrt, T. C. (2003). *Microbes Infect*. 5, 159-167).

If an individual has TB disease, i.e., has active TB, the individual typically is administered a combination of several drugs. It is very important, however, that the individual continue a correct treatment regimen for the full length of the treatment. If the drugs are taken incorrectly, or stopped, the individual can suffer a relapse and will be able to infect others with TB.

When an individual becomes sick with TB a second time, the TB infection may be more difficult to treat because the TB bacteria have become drug resistant, i.e., TB bacteria in the body are unaffected by some drugs used to treat TB. Multidrug-resistant tuberculosis (MDR TB) is a very dangerous form of tuberculosis. In particular, some TB bacteria become resistant to the effects of various anti-TB drugs, and these resistant TB bacteria then can cause TB disease. Like regular TB, MDR TB can be spread to others.

To avoid drug resistance in the treatment of TB, a four-drug regimen, i.e., isoniazid, rifampin, pyrazinamide, and streptomycin, is administered to TB patients. Aminoglycosides, such as streptomycin, are important anti-TB agents, but their utility is restricted by the requirement of parenteral administration, which is inconvenient and leads to poor patient compliance. It is theorized that poor patient compliance also can lead to the development of drug resistance, and it appears that the frequency of streptomycin resistance among anti-TB drugs is surpassed only by isoniazid.

In view of the above, an urgent need exists for new anti-TB agents useful in an effective treatment regimen for both the active and latent TB, and that effectively treat TB caused by multidrug resistant (MDR) strains of bacteria. Therefore, it would be advantageous to provide compounds and compositions for administration to an individual in the treatment of tuberculosis.

Figure 4:
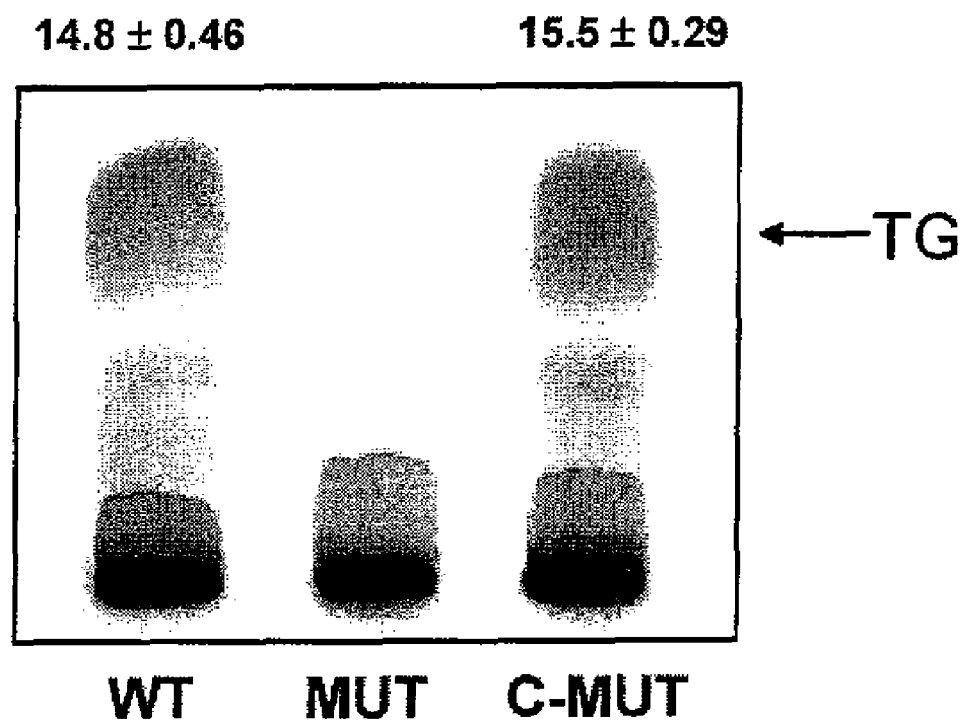

FIG. 4. TG accumulation in *M. tuberculosis* (WT), tgs1 mutant (MUT) and complemented tgs1 mutant (C-MUT) after 16 days under hypoxia. Same proportion of lipids were separated by TLC using n-hexane:diethyl ether (9:1, v/v) and lipids were visualized by dichromate/sulfuric acid charring. Charred TLC chromatogram is shown from a typical experiment and the intensity of the TG band was determined in arbitrary units by the AlphaImager 2200 Gel Doc system. The values are given as ±SEM of three independent measurements.

Figure 5:
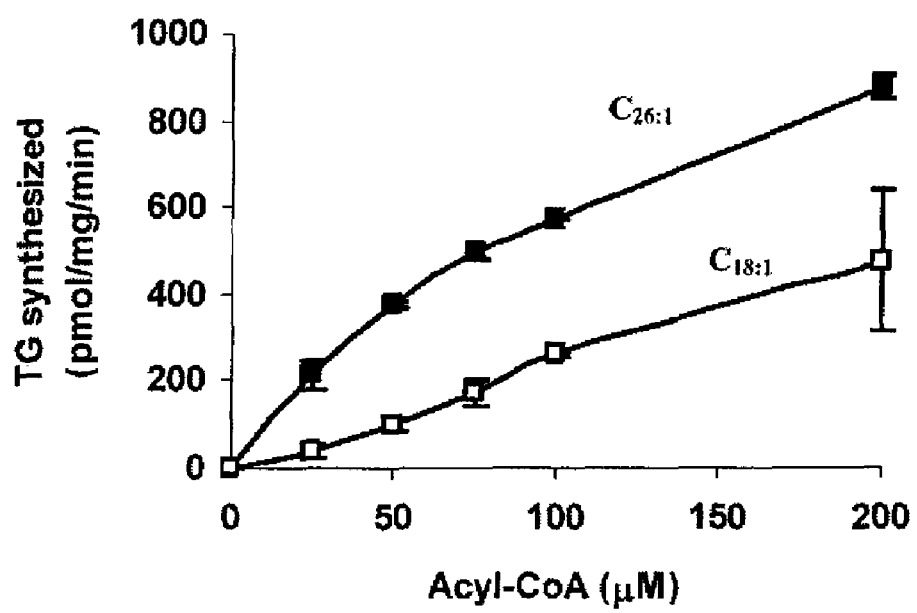
Figure 5:
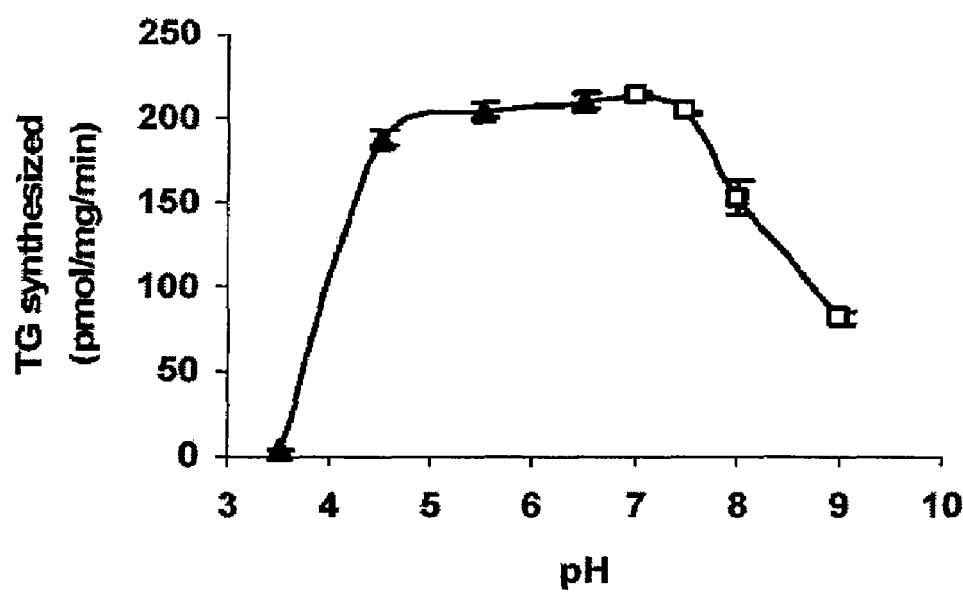

FIG. 5. Effects of acyl chain-length and pH on TG synthesis by recombinant TGS1. A, total cell lysate of *E. coli* expressing TGS1 was assayed for TGS activity using $C_{26:0}$-CoA (■) and $C_{18:1}$-CoA (□). B, Effect of pH on TGS activity Assays were done in 0.1 M citrate-phosphate buffer pH 3.5/4.5/5.5/6.5 (▲) or 0.1 M Tris-HCl pH 7.0/7.5/8.0/9.0 (□).

Figure 6:
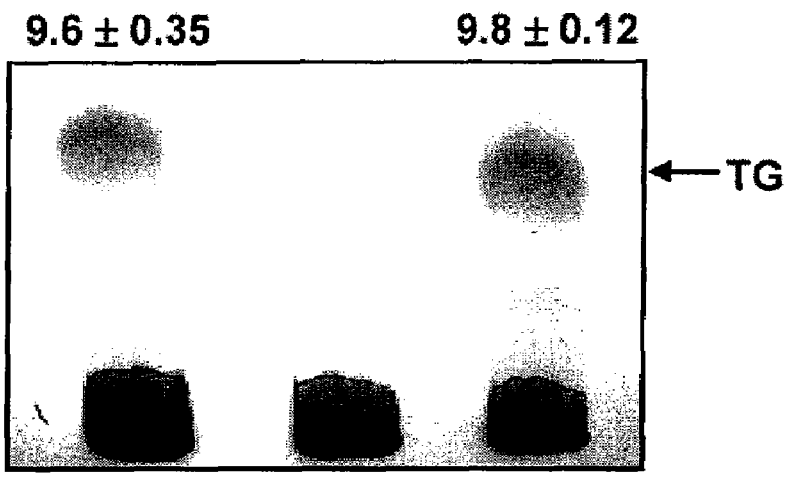
Figure 6:
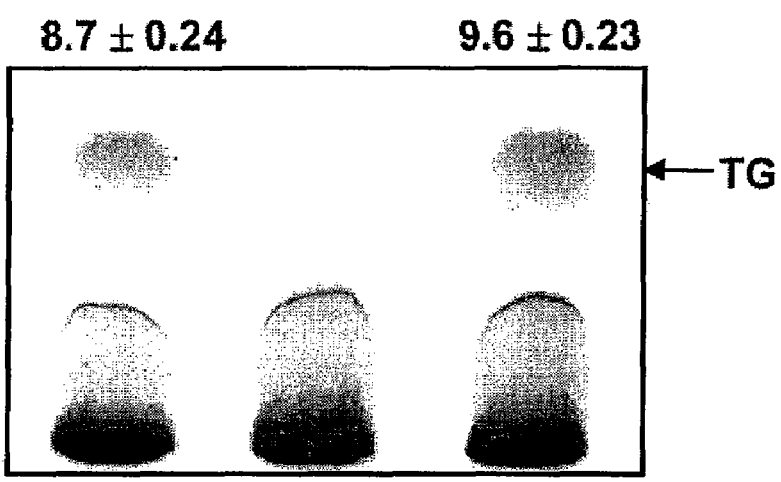
Figure 6:
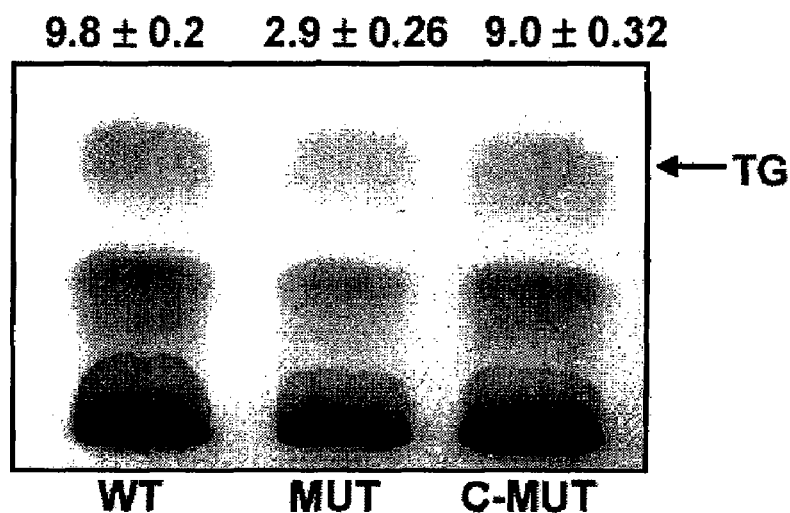

FIG. 6. Dichromate-sulphuric acid charring of lipids showing TG accumulation in *M. tuberculosis* grown under stress conditions. Total lipids extracted from wild type (WT), tgs1 mutant (MUT) and complemented tgs1 mutant (C-MUT) under A, low pH growth, B, static growth and C, upon NO treatment. In each case same proportion of lipids were separated by TLC using n-hexane:diethyl ether (9:1, v/v). Charred TLC chromatograms are shown from a typical experiment and the intensity of the TG band was determined in arbitrary units by the AlphaImager 2200 Gel Doc system. The values are given as ±SEM of three independent measurements.

Figure 7:
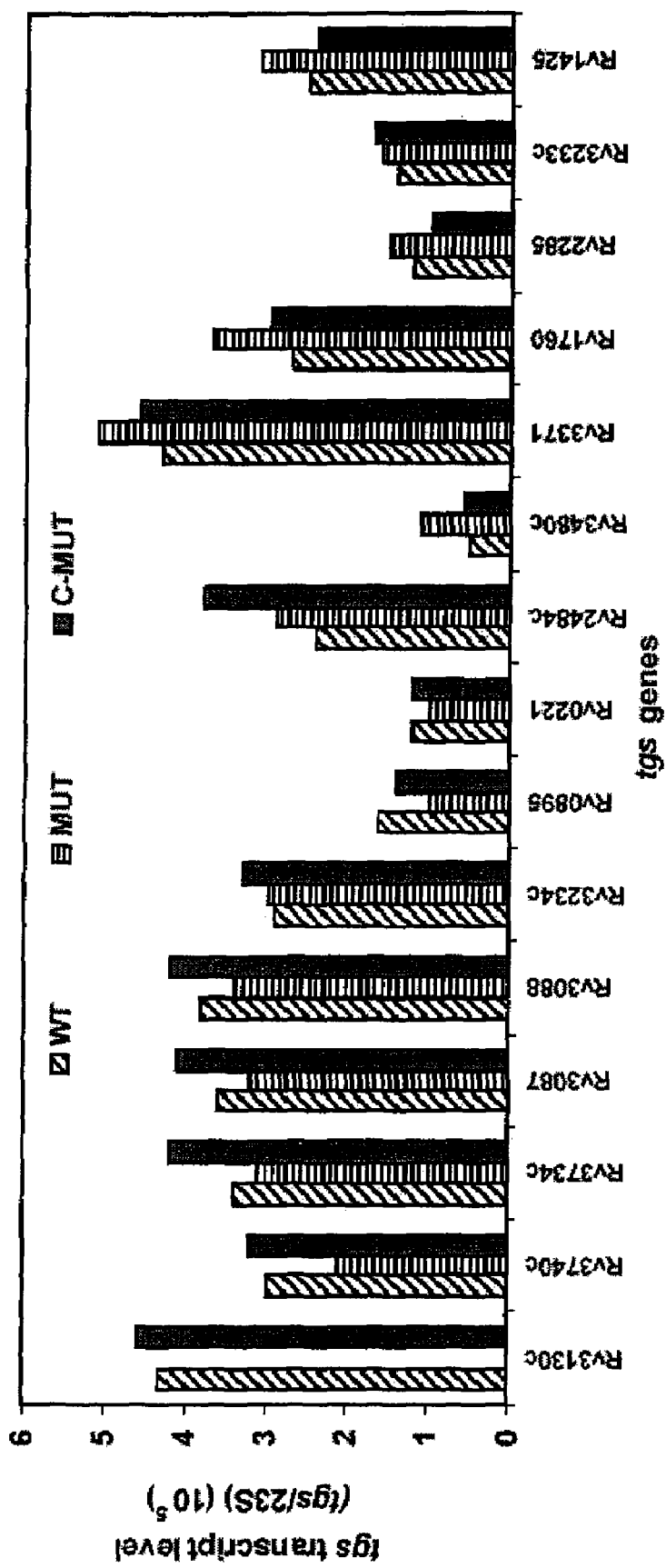

FIG. 7. Induction of tgs genes in *M. tuberculosis* strains by NO treatment. Transcript levels were measured by semiquantitative RT-PCR and expressed as a fraction of the 23S rRNA transcript level. WT, wild type; MUT, tgs1 mutant; C-MUT, tgs1-complemented strain.

DETAILED DESCRIPTION

The ability of *Mycobacterium tuberculosis* to go into a latent/dormant state and survive under such conditions for decades make TB control extremely difficult. Developing drugs targeted at the ability of the pathogen to survive under such latent conditions for long periods is one way to fight against latent TB. The invention is based, in part, on the inventors discovery of a novel TB gene (Rv3l 30c) encoding an enzyme required for *Mycobacterium tuberculosis* to store energy in order to enter and survive the dormancy (or latent) period. The gene sequence is provided as SEQ ID NO: 1. The inventors have discovered that triacyiglycerol (TG) can be used as an energy source by *M. tuberculosis* during the dormancy period, thus its synthesis could be an ideal drug target against latent TB. SEQ ID NO: 2 shows one example of a *M. tuberculosis* TG storage (MTTGS) polypeptide. Polypeptides useful in accordance with the teachings herein is further described herein. MTTGS polynucleotides and polypeptides as described herein may be implemented to identify compounds to treat TB.

Thus, according to one embodiment, the invention pertains to a method of screening for therapeutic agents useful in the treatment of *Mycobacterium tuberculosis* infection in a mammal comprising the steps of i) contacting a test compound with a MTTGS polypeptide, ii) detecting binding of said test compound to said MTTGS polypeptide.

Another embodiment of the subject invention pertains to a method of screening for therapeutic agents useful in the treatment of *Mycobacterium tuberculosis* infection in a mammal comprising the steps of i) determining the activity of a MTTGS polypeptide at a certain concentration of a test compound or in the absence of said test compound, ii) determining the activity of said polypeptide at a different concentration of said test compound.

1. Screening Methods

The invention provides assays for screening test compounds which bind to or modulate the activity of an MTTGS polypeptide or bind to and inhibit or affect expression of an MTTGS polynucleotide. A test compound preferably binds to an MTTGS polypeptide. More preferably, a test compound decreases or increases MTTGS activity by at least about 10, preferably about 50, more preferably about 75, 90, or 100% relative to the absence of the test compound.

1.1. Test Compounds

Test compounds relate to agents that potentially have therapeutic activity, i.e., bind to or modulate the activity of an MTTGS polypeptide or bind to or affect expression of an MTTGS polynucleotide. Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Methods for the synthesis of molecular libraries are well known in the art (see, for example, DeWitt et al., Proc. Natl. Acad. Sci. U.S.A. 90, 6909, 1993; Erb et al. Proc. NatL. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994).

1.2. High Throughput Screening

Test compounds can be screened for the ability to bind to and inhibit MTTGS polypeptides or polynucleotides or to affect MTTGS activity or MTTGS gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 µl. In addition to the plates, many instruments, materials, pipettors, robotics, plate washers, and plate readers are commercially available to fit the 96-well format. Alternatively, "free format assays," or assays that have no physical barrier between samples, can be used.

1. 3. Binding Assays

For binding assays, the test compound is preferably, but not necessarily, a small molecule which binds to and occupies, for example, the active site of the MTTGS polypeptide, such that normal biological activity is prevented. Examples of such small molecules include, but are not limited to, small peptides or peptide-like molecules.

In binding assays, either the test compound or the MTTGS polypeptide can comprise a detectable label, such as a fluorescent, radioisotopic, chemiluminescent, or enzymatic label, such as horseradish peroxidase, alkaline phosphatase, or luciferase. Detection of a test compound which is bound to the MTTGS polypeptide can then be accomplished, for example, by direct counting of radioemission, by scintillation counting, or by determining conversion of an appropriate substrate to a detectable product.

Those skilled in the art equipped with teachings herein will appreciate that there are multiple conventional methods of detecting binding of a test compound. For example, binding of a test compound to a MTTGS polypeptide can be determined without labeling either of the interactants. A microphysiometer can be used to detect binding of a test compound with an MTTGS polypeptide. A microphysiometer (e.g., CYTOSENSOR™) is an analytical instrument that measures the rate at which a cell acidifies its environment using a light-addressable potentiometric sensor (LAPS). Changes in this acidification rate can be used as an indicator of the interaction between a test compound and an MTTGS polypeptide (McConnell et al., Science 257, 19061912, 1992).

In another alternative example, determining the ability of a test compound to bind to an MTTGS polypeptide can be accomplished using a technology such as real-time Bimolecular Interaction Analysis (BIA) (Sjolander & Urbaniczky, Anal Chem. 63, 23382345, 1991, and Szabo et al., Curr. Opin. Struct. Biol. 5, 699705, 1995). BIA is a technology for studying biospecific interactions in real time, without labeling any of the interactants (e.g., BIAcore™.). Changes in the optical phenomenon surface plasmon resonance (SPR) can be used as an indication of real-time reactions between biological molecules.

In yet another aspect of the invention, an MTTGS polypeptide can be used as a "bait protein" in a two-hybrid assay or three-hybrid assay (see, e.g., U.S. Pat. No. 5,283,317; Zervos et al., Cell 72, 223232, 1993; Madura et al., J. Biol. Chem. 268, 1204612054, 1993; Bartel et al., BioTechniques 14, 920924, 1993; Iwabuchi et al., Oncogene 8, 16931696, 1993; and Brent WO94/10300), to identify other proteins which bind to or interact with the MTTGS polypeptide and modulate its activity.

In many screening embodiments, it may be desirable to immobilize either the MTTGS polypeptide (or polynucleotide) or the test compound to facilitate separation of bound from unbound forms of one or both of the interactants, as well as to accommodate automation of the assay. Thus, either the MTTGS polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the MTTGS polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a MTTGS polypeptide (or polynucleotide) can be accomplished in any vessel suitable for containing the reactants. Examples of such vessels include microtiter plates, test tubes, and microcentrifuge tubes.

In a specific embodiment, the MTTGS polypeptide may be a fusion protein comprising a domain that allows the MTTGS polypeptide to be bound to a solid support. For example, glutathione S-transferase fusion proteins can be adsorbed onto glutathione sepharose beads (Sigma Chemical, St. Louis, Mo.) or glutathione derivatized microtiter plates, which are then combined with the test compound or the test compound and the nonadsorbed MTTGS polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a MTTGS polypeptide (or polynucleotide) or a test compound can be immobilized utilizing conjugation of biotin and streptavidin. Biotinylated MTTGS polypeptides (or polynucleotides) or test compounds can be prepared from biotinNHS(Nhydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a MTTGS polypeptide, polynucleotide, or a test compound, but which do not interfere with a desired binding site, such as the active site of the MTTGS polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the MTTGS polypeptide or test compound, enzyme-linked assays which rely on detecting an activity of the MTTGS polypeptide, and SDS gel electrophoresis under non-reducing conditions.

Screening for test compounds which bind to a MTTGS polypeptide or polynucleotide also can be carried out in an intact cell. Any cell which comprises a MTTGS polypeptide or polynucleotide can be used in a cell-based assay system. A MTTGS polynucleotide can be naturally occurring in the cell or can be introduced using techniques such as those described above. Binding of the test compound to a MTTGS polypeptide or polynucleotide is determined as described above.

1.4. Enzyme Assays

Test compounds can be tested for the ability to increase or decrease the TGS activity of a MTTGS polypeptide. TGS activity can be measured, for example, by adapting techniques such as that described in U.S. Pat. No. 4,529,693 (see Example 2). Enzyme assays can be carried out after contacting either a purified MTTGS polypeptide, a cell membrane preparation, or an intact cell with a test compound. A test compound which decreases TGS activity of a MTTGS polypeptide by at least about 10, preferably about 50, more preferably about 75, 90, or 100% is identified as a potential therapeutic agent for decreasing MTTGS activity. A test compound which increases TGS MTTGS polypeptide by at least about 10, preferably about 50, more preferably about 75, 90, or 100% is identified as a potential therapeutic agent for increasing TGS activity.

1.5. Gene Expression

In another embodiment, test compounds which increase or decrease MTTGS gene expression are identified. An MTTGS polynucleotide is contacted with a test compound, and the expression of an RNA or polypeptide product of the MTTGS polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of MTTGS mRNA or polypeptide expression in the cells can be determined by methods well known in the art for detecting mRNA or polypeptide. Either qualitative or quantitative methods can be used. The presence of polypeptide products of an MTTGS polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a MTTGS polypeptide.

Such screening can be carried out either in a cell-free assay system or in an intact cell. Any cell which expresses a MTTGS polynucleotide can be used in a cell-based assay system. The MTTGS polynucleotide can be naturally occurring in the cell or can be introduced using techniques such as those described above. Either a primary culture or an established cell line, such as CHO or human embryonic kidney 293 cells, can be used.

2. Pharmaceutical Compositions

The invention also pertains to pharmaceutical compositions comprising one or more therapeutic agents that are identified by screening methods that utilize MTTGS polypeptides and/or polynucleotides. Therapeutic agent(s) can be administered to a patient to achieve a therapeutic effect, i.e. useful in treatment of TB. Pharmaceutical compositions of the invention can comprise, for example, therapeutic agents identified by a screening method embodiment described herein, which are identified by their ability to bind to or affect activity of MTTGS polypeptides, or bind to and/or affect expression MTTGS polynucleotides. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Further details on techniques for formulation and administration can be found in the latest edition of REMINGTON'S PHARMACEUTICAL SCIENCES (Maack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

This invention further pertains to the use of novel agents identified by the screening assays described above. Accordingly, it is within the scope of this invention to use a therapeutic agent identified as described herein in an appropriate animal model. For example, an agent identified as described herein (for example, but not limited to., a modulating agent, an antisense nucleic acid molecule, a specific antibody, ribozyme, or a MTTGS polypeptide binding molecule) can be used in an animal model to determine the efficacy, toxicity, or side effects of treatment with such an agent. Furthermore, this invention pertains to uses of novel agents identified by the above described screening assays for treatments as described herein.

Those skilled in the art will appreciate that numerous delivery mechanisms are available for delivering a therapeutic agent to an area of need. By way of example, the agent may be delivered using a liposome as the delivery vehicle. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. A liposome useful in the present invention comprises a lipid composition that is capable of fusing with the plasma membrane of the targeted cell to deliver its contents to the cell.

Preferably, the transfection efficiency of a liposome is about 0.5 µg of DNA per 16 nmole of liposome delivered to about 106 cells, more preferably about 1.0 µg of DNA per 16 nmole of liposome delivered to about $10^6$ cells, and even more preferably about 2.0 µg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 μg to about 10 μg of polynucleotide is combined with about 8 nmol of liposomes, more preferably from about 0.5 μg to about 5 μg of polynucleotides are combined with about 8 nmol liposomes, and even more preferably about 1.0 μg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. Trends in Biotechnol. 11, 202-05 (1993); Chiou et al., GENE THERAPEUTICS: METHODS AND APPLICATIONS OF DIRECT GENE TRANSFER (J. A. Wolff, ed.) (1994); Wu & Wu, J. Biol. Chem. 263, 621-24 (1988); Wu et al., J. Biol. Chem. 269, 542-46 (1994); Zenke et al., Proc. Natl. Acad. Sci. U.S.A. 87, 3655-59 (1990); Wu et al., J. Biol. Chem. 266, 338-42 (1991).

2.1 Determination of a Therapeutically Effective Dose

The determination of a therapeutically effective dose of therapeutic agents identified by a screening method herein is well within the capability of those skilled in the art. A therapeutically effective dose refers to that amount of active ingredient which attenuates or eliminates TB infection contrasted to TB infection or attenuation that occurs in the absence of the therapeutically effective dose.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Preferably, an therapeutic agent reduces expression of an MTTGS gene or the activity of an MTTGS polypeptide by at least about 10, preferably about 50, more preferably about 75, 90, or 100% relative to the absence of the reagent. The effectiveness of the mechanism chosen to decrease the level of expression of an MTTGS gene or the activity of an MTTGS polypeptide can be assessed using methods well known in the art, such as hybridization of nucleotide probes to MTTGS-specific mRNA, quantitative RT-PCR, immunologic detection of an MTTGS polypeptide, or measurement of MTTGS activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Any of the therapeutic methods described above can be applied to any subject in need of such therapy.

3. Polypeptides

*M. tuberculosis* TG storage (MTTGS) polypeptides according to the invention comprise at least 12, 15, 25, 50, 75, 100, 125, 150, 175, 200, 225, 250 or 265 contiguous amino acids selected from the amino acid sequence shown in SEQ ID NO: 2, or a biologically active variant thereof, as defined below. A MTTGS polypeptide of the invention therefore can be a portion of an MTTGS protein, a full-length MTTGS protein, or a fusion protein comprising all or a portion of MTTGS protein.

3.1 Biologically Active Variants

MTTGS polypeptide variants which are biologically active, i.e., confer an ability by *M. tuberculosis* to store and/or process TG, also are considered MTTGS polypeptides for purposes of this application. Preferably, naturally or non-naturally occurring MTTGS polypeptide variants have amino acid sequences which are at least about 55, 60, 65, or 70, preferably about 75, 80, 85, 90, 96, 96, or 98% identical to the amino acid sequence shown in SEQ ID NO: 2 or a fragment thereof. Percent identity between a putative MTTGS polypeptide variant and an amino acid sequence of SEQ ID NO: 2 is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of an MTTGS polypeptide can be found using computer programs well known in the art, such as DNASTAR software. Whether an amino acid change results in a biologically active MTTGS polypeptide can readily be determined by assaying for MTTGS activity, as described for example, in the specific Examples, below.

3.2 Fusion Proteins

In some embodiments of the invention, it is useful to create fusion proteins. By way of example, fusion proteins are useful for generating antibodies against MTTGS polypeptide amino acid sequences and for use in various assay systems. For example, fusion proteins can be used to identify proteins which interact with portions of an MTTGS polypeptide. Protein affinity chromatography or library-based assays for protein—protein interactions, such as the yeast two-hybrid or phage display systems, can be used for this purpose. Such methods are well known in the art and also can be used as drug screens.

A MTTGS polypeptide fusion protein comprises two polypeptide segments fused together by means of a peptide bond. For example, the first polypeptide segment can comprise at least 12, 15, 25, 50, 75, 100, 125, 150, 175, 200, 225, or 250 contiguous amino acids of SEQ ID NO: 2 or of a biologically active variant, such as those described above. The first polypeptide segment also can comprise full-length MTTGS protein.

The second polypeptide segment can be a full-length protein or a protein fragment. Proteins commonly used in fusion protein construction include galactosidase, glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the MTTGS polypeptide-encoding sequence and the heterologous protein sequence, so that the MTTGS polypeptide can be cleaved and purified away from the heterologous moiety.

Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

3.3 Obtaining Polypeptides

MTTGS polypeptides can be obtained, for example, by purification of polypeptides from *M. tuberculosis*, expressed by of MTTGs polynucleotide(s) and other appropriate methods as will be appreciated by those skilled in the art in view of the teachings herein.

3.4 Protein Purification

MTTGS polypeptides can be purified from any cell which expresses the enzyme, including host cells which have been transfected with MTTGS enzyme expression constructs. A purified MTTGS enzyme polypeptide is separated from other compounds which normally associate with the MTTGS enzyme polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified MTTGS polypeptides is at least 80% pure; preferably, the preparations are 90%, 95%, or 99% pure. Purity of the preparations can be assessed by any means known in the art, such as SDS-polyacrylamide gel electrophoresis.

4. Polynucleotides

An MTTGS polynucleotide can be single- or double-stranded and comprises a coding sequence or the complement of a coding sequence for an MTTGS polypeptide. A coding sequence for MTTGS polypeptide of SEQ ID NO: 2 is shown in SEQ ID NO: 1.

Degenerate nucleotide sequences encoding MTTGS polypeptides, as well as homologous nucleotide sequences which are at least about 50, 55, 60, 65, 60, preferably about 75, 90, 96, or 98% identical to the nucleotide sequence shown in SEQ ID NO: 1 also are triaglycerol synthase-like enzyme polynucleotides. Percent sequence identity between the sequences of two polynucleotides is determined using computer programs such as ALIGN which employ the FASTA algorithm, using an affine gap search with a gap open penalty of -12 and a gap extension penalty of -2. Complementary DNA (cDNA) molecules, species homologs, and variants of MTTGS polynucleotides which encode biologically active MTTGS polypeptides also are MTTGS polynucleotides.

4.1 Identification of Polynucleotide Variants and Homologs

Variants and homologs of the MTTGS polynucleotides described above also are MTTGS polynucleotides. Typically, homologous MTTGS polynucleotide sequences can be identified by hybridization of candidate polynucleotides to known MTTGS polynucleotides under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each homologous sequences can be identified which contain at most about 25-30% basepair mismatches. More preferably, homologous nucleic acid strands contain 15-25% basepair mismatches, even more preferably 5-15% basepair mismatches.

Species homologs of the MTTGS polynucleotides disclosed herein also can be identified by making suitable probes or primers and screening cDNA expression libraries. It is well known that the Tm of a double-stranded DNA decreases by 1-1.5° C. with every 1% decrease in homology (Bonner et al., J. Mol. Biol. 81, 123 (1973). Variants of MTTGS polynucleotides or polynucleotides of other species can therefore be identified by hybridizing a putative homologous MTTGS polynucleotide with a polynucleotide having a nucleotide sequence of SEQ ID NO: 1 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to MTTGS polynucleotides or their complements following stringent hybridization and/or wash conditions also are MTTGS polynucleotides. Stringent wash conditions are well known and understood in the art and are disclosed, for example, in Sambrook et al., MOLECULAR CLONING: A LABORATORY MANUAL, $2^{nd}$ ed., 1989, at pages 9.50-9.51.

Typically, for stringent hybridization conditions a combination of temperature and salt concentration should be chosen that is approximately 12-20° C. below the calculated $T_m$ of the hybrid under study. The $T_m$ of a hybrid between an MTTGS polynucleotide having a nucleotide sequence shown in SEQ ID NO: 1 or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$$T_m = 81.5° C. - 16.6(\log_{10}[Na^+]) + 0.41(\% G+C) - 0.63(\% \text{formamide}) - 600/l,$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

4.2 Preparation of Polynucleotides

A naturally occurring MTTGS polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated MTTGS polynucleotides. For example, restriction enzymes and probes can be used to isolate polynucleotide fragments which comprises MTTGS nucleotide sequences. Isolated polynucleotides are in preparations which are free or at least 70, 80, or 90% free of other molecules.

MTTGS DNA molecules can be made with standard molecular biology techniques, using MTTGS mRNA as a template. MTTGS DNA molecules can thereafter be replicated using molecular biology techniques known in the art and disclosed in manuals such as Sambrook et al. (1989). An amplification technique, such as PCR, can be used to obtain additional copies of polynucleotides of the invention. The inventors have successfully demonstrated this approach.

Alternatively, synthetic chemistry techniques can be used to synthesizes MTTGS polynucleotides. The degeneracy of the genetic code allows alternate nucleotide sequences to be synthesized which will encode a MTTGS polypeptide having, for example, an amino acid sequence shown in SEQ ID NO: 2 or a biologically active variant thereof.

4.3 Expression of Polynucleotides

To express a MTTGS polynucleotide, the polynucleotide can be inserted into an expression vector which contains the necessary elements for the transcription and translation of the inserted coding sequence. Methods which are well known to those skilled in the art can be used to construct expression vectors containing sequences encoding MTTGS polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a MTTGS enzyme polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those nontranslated regions of the vector enhancers, promoters, 5' and 3' untranslated regions which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding an MTTGS polypeptide, vectors based on SV40 or EBV can be used with an appropriate selectable marker.

5. Host Cells

According to certain embodiments of the subject invention, an MTTGS polynucleotide will need to be inserted into a host cell, for expression, processing and/or screening. A host cell strain can be chosen for its ability to modulate the expression of the inserted sequences or to process the expressed MTTGS polypeptide in the desired fashion. Such modifications of the polypeptide include, but are not limited to, acetylation, carboxylation, glycosylation, phosphorylation, lipidation, and acylation. Posttranslational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

Stable expression is preferred for long-term, high yield production of recombinant proteins. For example, cell lines which stably express MTTGS polypeptides can be transformed using expression vectors which can contain viral origins of replication and/or endogenous expression elements and a selectable marker gene on the same or on a separate vector. Following the introduction of the vector, cells can be allowed to grow for 12 days in an enriched medium before they are switched to a selective medium. The purpose of the selectable marker is to confer resistance to selection, and its presence allows growth and recovery of cells which successfully express the introduced MTTGS sequences. Resistant clones of stably transformed cells can be proliferated using tissue culture techniques appropriate to the cell type. See, for example, ANIMAL CELL CULTURE, R. I. Freshney, ed., 1986.

5.1 Detecting Expression

A variety of protocols for detecting and measuring the expression of a MTTGS polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a MTTGS polypeptide can be used, or a competitive binding assay can be employed. These and other assays are described in Hampton et al., SEROLOGICAL METHODS: A LABORATORY MANUAL, APS Press, St. Paul, Minn., (1990) and Maddox et al., J. Exp.

5.2 Expression and Purification of Polypeptides

Host cells transformed with nucleotide sequences encoding MTTGS polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode MTTGS polypeptides can be designed to contain signal sequences which direct secretion of soluble MTTGS polypeptides through a prokaryotic or eukaryotic cell membrane or which direct the membrane insertion of membrane-bound MTTGS polypeptide.

6. Antibodies

Antibodies are referenced herein and various aspects of the subject invention utilize antibodies specific to MTTGS polypeptide(s). As described above, one example of a therapeutic agent may pertain to an antibody. Any type of antibody known in the art can be generated to bind specifically to an epitope of an MTTGS polypeptide. "Antibody" as used herein includes intact immunoglobulin molecules, as well as fragments thereof, such as Fab, F(ab')$_2$, and Fv, which are capable of binding an epitope of an MTTGS polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of an MTTGS polypeptide can be used therapeutically, as mentioned, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen. Antibodies useful for embodiments of the subject invention may be polyclonal, but are preferably monoclonal antibodies.

7. Ribozymes

Ribozymes may be one category of test compounds potentially useful as therapeutic agents for treatment of TB infection. Ribozymes are RNA molecules with catalytic activity. See, e.g., Cech, Science 236, 15321539; 1987; Cech, Ann. Rev. Biochem. 59, 543568; 1990, Cech, Curr. Opin. Struct. Biol. 2, 605609; 1992, Couture & Stinchcomb, Trends Genet. 12, 510515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

Accordingly, another aspect of the invention pertains to using the coding sequence of a MTTGS polynucleotide to generate ribozymes which will specifically bind to mRNA transcribed from the MTTGS polynucleotide. Methods of designing and constructing ribozymes which can cleave other RNA molecules in trans in a highly sequence specific manner have been developed and described in the art (see Haseloff et al. Nature 334, 585591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a MTTGS RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate MTTGS RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease MTTGS expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of mRNA occurs only when both a ribozyme and a target gene are induced in the cells.

8. TGS1 Deficiency Abolishes TG Accumulation Under Conditions that Lead to Dormancy-like State, and that Complementation Restores TG Accumulation

8.1 Introduction

Tuberculosis (TB), one of the biggest killers among the infectious diseases, poses a major public health problem mostly in the developing world with 8 million new TB cases and 2 million deaths a year (33, 35). *Mycobacterium tuberculosis*, the causative agent of TB, is inhaled by people emanating as aerosol from active TB patients. Usually only a small fraction of the people (about 5%) thus infected develop active TB, while the rest carry latent infection for the rest of their lives until reactivation of the pathogen occurs upon weakening of the immune system. Thus, AIDS causes reactivation of the latent tubercule bacillus leading to rapid bacillary growth and dissemination resulting in the development of active TB (5, 11, 29, 34). The ability of the pathogen to go into a latent/dormant non-replicating state with very low metabolic activity and resistance to all of the currently available antituberculosis drugs (34, 35) makes TB eradication an extremely difficult challenge.

The metabolic and physiological state of the dormant pathogen that allows it to survive inside the host for decades remains unclear. There is strong evidence that fatty acids are the energy source to be used by the pathogen for its long term survival during the persistence phase of infection (11, 23). In *M. tuberculosis*, two genes icl1 and icl2 encode isocitrate lyase (ICL)—a key metabolic enzyme involved in fatty acid utilization. It was recently shown that deletion of both icl1 and icl2, but not deletion of either one, resulted in complete impairment of intracellular replication in macrophages and rapid elimination from the mouse lungs (19). Chemical inhibition of both ICL1 and ICL2 also blocked the growth of *M. tuberculosis* on fatty acids and in macrophages. However the source of the fatty acids remains unknown (19, 23). Recently, the inventors have shown that *M. tuberculosis* can synthesize and store triacylglycerol (TG) as an energy reserve under hypoxia and NO treatment, the stress conditions that lead to a dormancy-like state in culture (6). Intracellular TG inclusion bodies found in the pathogen (*M. tuberculosis*) obtained from organ lesions (10) and decrease of TG levels by growth of *M. bovis* BCG in macrophages (13) suggest that TG is used as an energy source for intracellular growth of the pathogen. The genes that could be involved in the synthesis of TG in the pathogen were recently identified. The inventors found 15 members of a novel class of diacylglycerol acyltransferase genes designated tgs (triacylglycerol synthase) (6) based on homology to such genes identified in *Acinetobacter calcoaceticus* (14). Which, if any of these genes, encodes the enzyme(s) actually involved in TG synthesis has not been established. The inventors previously assessed the degree of upregulation of the putative tgs genes upon induction of dormancy-like conditions in culture. The inventors also determined the enzyme activity of the mycobacterial tgs products expressed in *Escherichia coli*. Based on these results, tgs1 appeared to have the highest potential to contribute to TG accumulation (6). In this report, it is shown that tgs1 deficiency abolishes TG accumulation under conditions that lead to dormancy-like state, and that complementation restores TG accumulation. It is also shown that TGS1 expressed in *E. coli*, preferentially uses $C_{26}$ fatty acyl-CoA for TG synthesis and that $C_{26}$ fatty acid, which is known to be produced by the fatty acid synthase of *M. tuberculosis* (15), found to be a major long chain fatty acid in the TG accumulated under conditions that lead to a dormancy-like state. This enzyme is highly active over a wide range of pH including the acidic conditions expected in the granuloma.

8.2 Materials and Methods

Bacterial strains, Growth media and Chemicals. *M. tuberculosis* H37Rv (ATCC 25618), tgs1 mutant and complemented strain were grown in Middlebrook 7H9 (Difco, Detroit, Mich.), in Dubos-Tween-albumin medium broth (Difco, Detroit, Mich.) and Sauton medium as previously described (6). *Escherichia coli* DH5α and HB101 strains (Life Technologies, Gaithersburg, Md.) were used for cloning and propagation of plasmids and phasmids. For selection of transformants, *E. coli* was grown in Luria-Bertani (LB) broth or agar. *M. smegmatis* mc$^2$155 was grown in liquid LB medium with 0.5% Tween 80 for competent cell preparation and in Middlebrook 7H9 broth with 0.05% Tween 80 for transduction. When required, antibiotics were added to the culture media at the following concentration: ampicillin, 100 μg/ml for *E. coli* ; hygromycin B, 150 μg/ml for *E. coli* or 75 μg/ml for *M. tuberculosis*; kanamycin, 50 μg/ml for *E. coli* or 20 μg/ml for *M. tuberculosis*. The NO donor (spermine NONOate) and its reference compound, spermine tetrahydrochloride were purchased from Alexis Corporation. Other chemicals and antibiotics were from Sigma Chemical Co. and Fisher Scientific. DNA restriction and modifying enzymes were obtained from New England Bio-labs (Beverly, Mass.).

Growth Conditions for *M. tuberculosis*. To mimic a dormancy-like state in culture, in vitro stress conditions such as hypoxia, NO treatment, low pH and static growth were used. For hypoxia and NO treatment, experiments were done as previously described (6). Resistance to isoniazid (0.4 μg/ml) and sensitivity to metronidazole (12 μg/ml) of hypoxic cultures were also tested (6). For low pH growth, *M. tuberculosis* cells were initially grown in Middlebrook 7H9 media until $OD_{600}$ of 0.6-0.8, and the cells were washed and suspended in Middlebrook 7H9 media, pH 5.0 and grown for three weeks in a roller bottle at 37° C. For growth under static condition, *M. tuberculosis* cells were grown for 2 weeks in Middlebrook 7H9 media until $OD_{600}$ of 1.6 and then the culture was kept standing for 1 week at 37° C. Cells collected at different time periods were used for RNA isolation and TG analysis.

Figure 1:
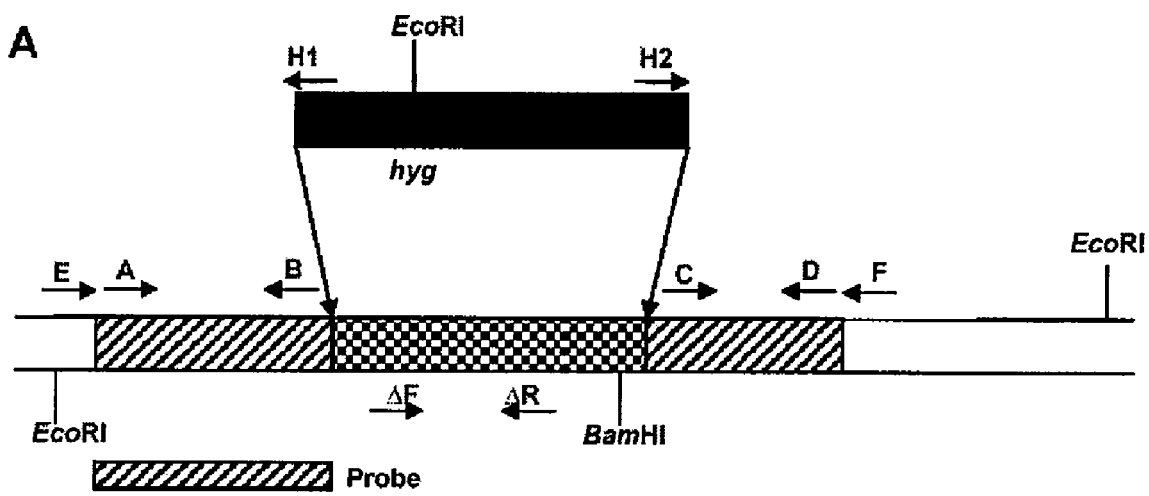
FIG. 1. Generation of a tgs1 mutant of *M. tuberculosis*. (A) Schematic representation of the disruption construct for tgs1. Hatched and checkered regions represent the regions used to make disruption construct. The checkered segment was replaced with hyg gene cassette (black box). Primers pairs E/H1, H2/F and ÄF/ÄR were used for PCR analysis of homologous recombination as described in text. (B) Southern blot hybridization of the wild type (WT) and three mutant clones (M1, M2 and M3). (C) RT-PCR analysis showing tgs1 transcript in wild type (WT) and tgs1-complemented strain (C-MUT), but not in tgs1 mutant (MUT).
Figure 1:
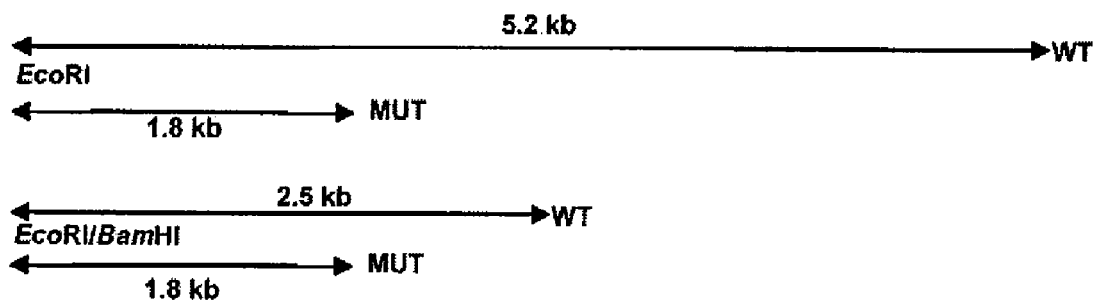
Figure 1:
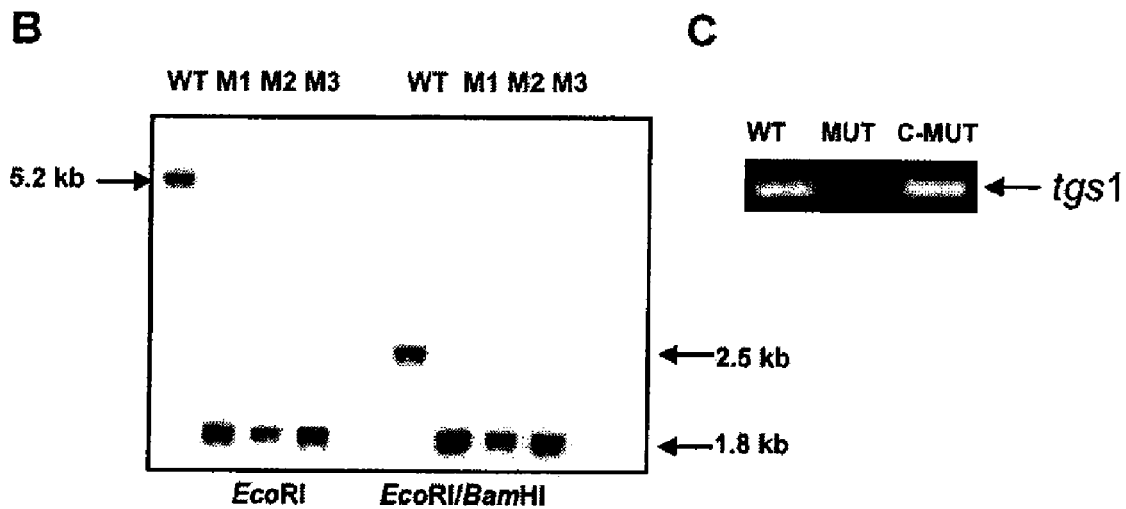
Figure 2:
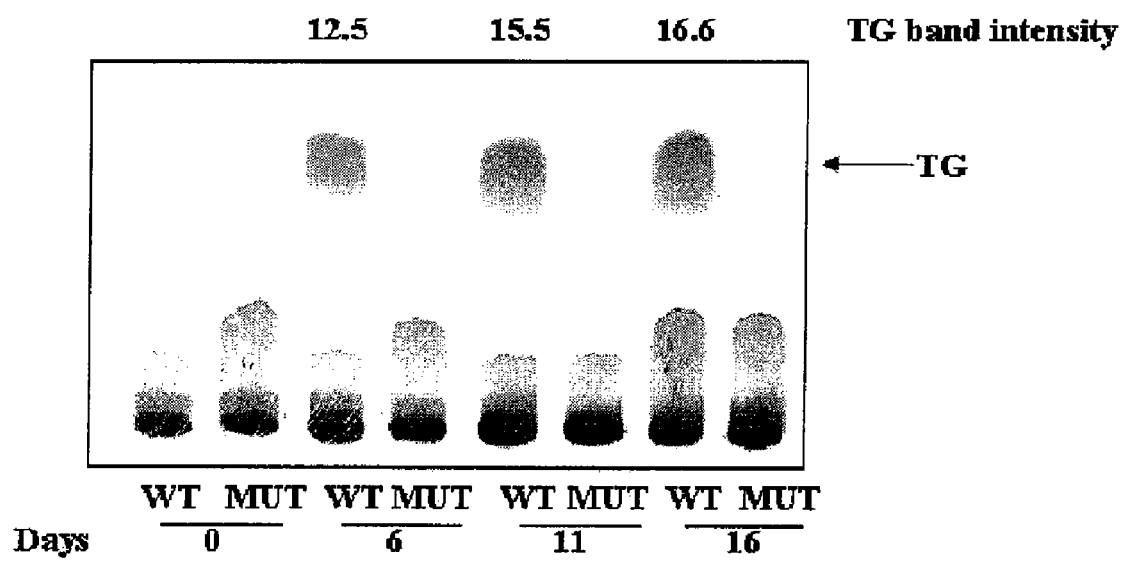
FIG. 2. Dichromate/sulphuric acid charring of lipids showing TG (triacylglycerol) accumulation in *M. tuberculosis* under hypoxia. At each time point total lipids were extracted from wild type *M. tuberculosis* (WT) and tgs1 mutant (MUT) (A) and after 6 h of incubation with 50 iM oleic acid-0.5% BSA (B). In each case same proportion of lipids were separated by TLC using n-hexane:diethyl ether (9:1, v/v). The intensity of the TG band determined in arbitrary units by Alphalmager 2200 Gel Doc system is shown on top of each panel.
Figure 2:
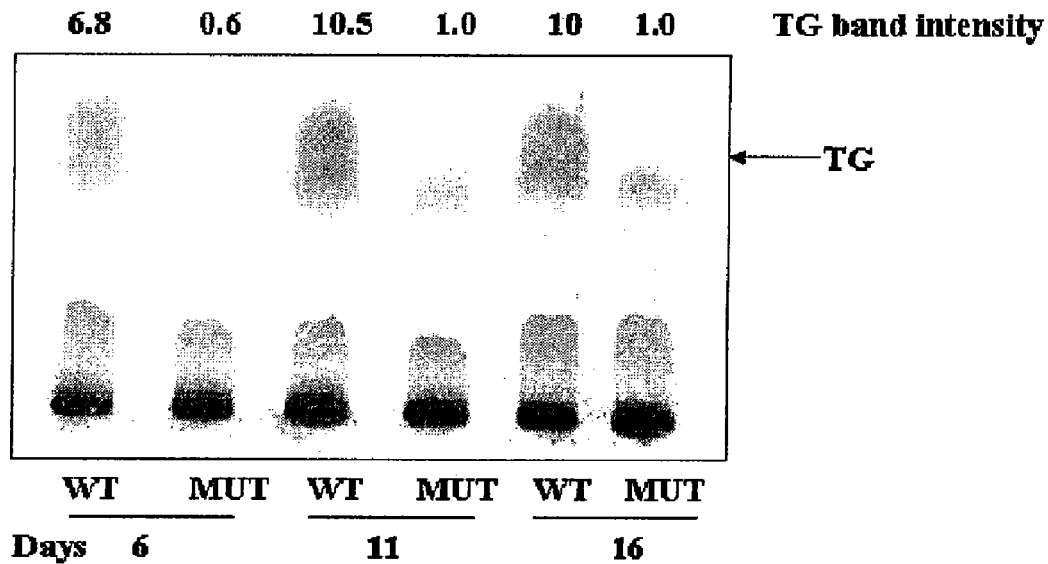
Figure 3:
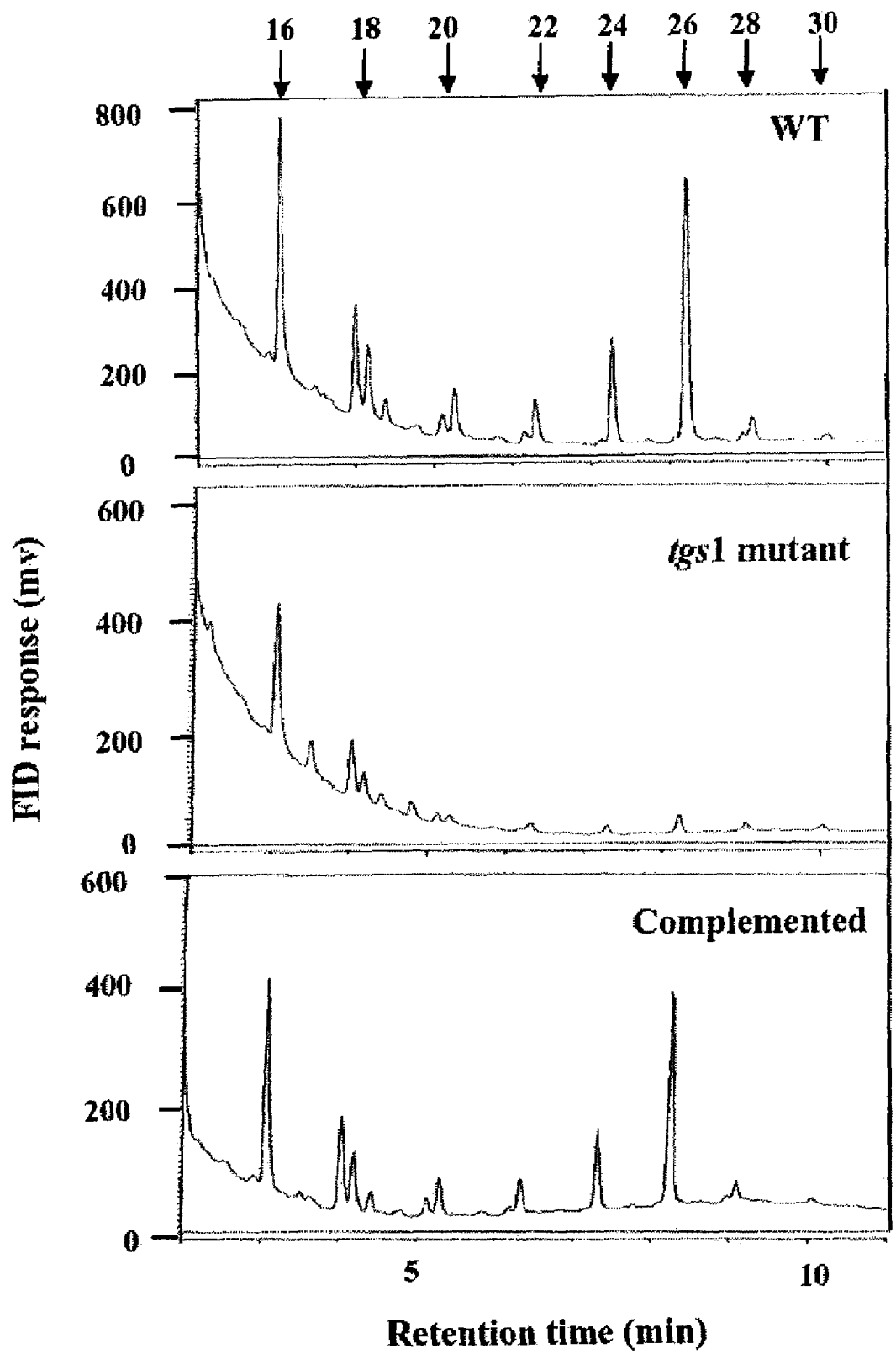
FIG. 3. GC analysis of fatty acids in TG from *M. tuberculosis* cells after 16 days under hypoxia. Methyl esters of fatty acid were prepared from TG recovered from TLC plates from the wild type, tgs1 mutant and complemented tgs1 mutant. Top, middle and bottom panel represent wild type (WT), tgs1 mutant and tgs1-complemented strain, respectively. Retention times of nfatty acids are indicated on top.

Generation of tgs1 Disrupted Mutant of *M. tuberculosis*. The general strategy used for gene disruption with the specialized transducing phage system was similar to that used previously (1, 28). tgs1 was disrupted by allelic exchange via specialized transduction using conditionally replicating mycobacteriophage phAE87. The disrupted copy of the gene was constructed by PCR amplification of the 5'-flanking and the 3'-flanking regions of the gene using *M. tuberculosis* DNA as a template and primer pairs introducing BspHI and PstI sites and XhoI and BspHI sites at the ends of the products, respectively (Table 1). Both products were then sequentially inserted on either side of the hygromycin resistance gene (hyg) cloned in vector pUC19. The 5'-flanking region consists of the first 10 bp of tgs1 and 784 bp sequence upstream of the gene. The 3'-flanking region contains the last 122 bp of tgs1 open reading frame (orf) and 667 bp downstream sequence. The disrupted copy of the gene was released by BspHI digestion cloned into pYUB572 which contains a bacteriophage lambda cos site and a PacI site. The recombinant cosmid was digested with PacI, ligated into the PacI site of phAE87 and the resultant recombinant phage was used to transduce wild type *M. tuberculosis*. Individual hygromycin resistant colonies were analyzed by PCR and Southern blot analysis to identify clones in which allelic exchange had occurred at the tgs1 locus. Several tgs1 mutants were screened by PCR analysis using specific primers located inside the deleted fragment of the gene (ΔF and ΔR) shown in Table 1. The allelic exchange by double cross-over was confirmed with two sets of primers, each representing a hyg primer (primers H1 and H2) and a primer (primers E and F) in the mycobacterial genome outside the gene sequence used for making the disruption construct (FIG. 1A).

Complementation of *M. tuberculosis* tgs1 Mutant. For complementation experiments, tgs1 coding sequence was amplified from genomic *M. tuberculosis* H37Rv DNA using Pfu Turbo Hotstart DNA Polymerase (Stratagene), and primers that introduced a KpnI site at both ends. The PCR product was cloned into pCR-Blunt II-TOPO (Invitrogen). After sequencing to confirm the absence of any mutations, the insert was excised from this vector by KpnI digestion and subcloned into KpnI-digested replicative shuttle vector pMIP12 for expression under the pBlaF* promoter (18). The construct was electroporated into the tgs1 disrupted mutant and transformants were selected on 7H11 plates with both kanamycin and hygromycin. Isolated colonies from the plates were checked for the expression of tgs1 by RT-PCR using primers shown in Table 1. RNA isolation and RT-PCR analysis were done as described previously (6).

Genomic DNA Isolation and Southern blotting. *M. tuberculosis* H37Rv genomic DNA was isolated by the GTC method using guanidine thiocyanate, Tris-HCl, Sarcosyl solution (7). DNA samples were digested with EcoRI and EcoRI/BamHI restriction enzymes, subjected to 1% agarose gel electrophoresis, transferred to Nylon membranes (Nytran Plus, Schleicher and Schuell, Keen, N.H.) and hybridized with [$\alpha$-$^{32}$ P]dCTP labeled probes using the random prime labeling system, rediprime II (Amersham Pharmacia Biotech, UK).

TG Analysis. *M. tuberculosis* wild type, tgs1 mutant and complemented strain of tgs1 cells were subjected to the desired stress and at defined experimental time points, cells were recovered by centrifugation, autoclaved and subjected to lipid extraction in chloroform: methanol (2:1, v/v) (28). In a separate set of hypoxia experiment, aliquots of the culture from *M. tuberculosis* wild type and tgs1 mutant taken at various time points were incubated with 50 μM oleic acid in 0.5% BSA solution and after 6 h of incubation, lipids were extracted for TG analysis. Total extracted lipids were separated by Silica G thin-layer chromatography (TLC) using n-hexane: diethylether (9:1, v/v) as solvent system. Dichromate/sulphuric acid charring of TLC plates was used to detect lipids. The charred TLC plates were also scanned for quantification of TG accumulation using the AlphaImager 2200 Gel Doc system (AlphaInnotech). Fatty acid methyl esters were prepared from TG by transesterification with 14% $BF_3$ in methanol and analyzed by gas chromatography (GC) using flame ionization detector response; the GC conditions for fatty acid methyl esters were the same as previously described (28). All stress growth experiments were repeated at least three times, and similar patterns were seen in all cases. Since details such as cell density were not absolutely identical in all repetitions, the average values and the results from a typical experiment are shown.

Enzyme Activity of TGS1 expressed in *E. coli* . TOSI was expressed in *E. coli* grown in Dual Media (Zymo Research, CA) for 12 h at 37° C. and total cell lysates were assayed for TGS activity. The assays were performed in 0.1 M citrate-phosphate buffer pH 6.5 containing 1 mg BSA, 10 mM $MgCl_2$, 14.5 μM [$^{14}$C]diolein (specific activity 55 Ci/mol, American Radiolabeled Chemicals), 500 μM diolein, indicated concentrations of oleoyl ($C_{18:1}$)-CoA or hexacosanoyl ($C_{26:0}$)-CoA and 100-200 μg of protein in a total volume of 250 μl for 2 h at 37° C. The pH dependence of TGS activity was determined by pre-incubating the total cell lysate containing the expressed TGS1 protein in appropriate buffer prior to assay using oleoyl-CoA as a model substrate. Following the assay, the reaction mixture was extracted and the TG product was quantified as described before (6).

8.3 Results

Disruption of tgs1 in *M. tuberculosis* and complementation of the disrupted mutant. On the basis of the enzymatic activities of expressed tgs gene products and the level of their induction as the pathogen entered a dormancy-like conditions, tgs1 appeared to be a prime candidate for involvement in TG synthesis (6). To test this possibility, the inventors generated a tgs1 disrupted mutant of *M. tuberculosis*. tgs1 was disrupted by allelic exchange via specialized transduction using conditionally replicating mycobacteriophage phAE87 (1). To prepare the tgs1 disruption construct a 1275 bp out of the total 1392 bp tgs1 orf was replaced with the hygromycin-resistance gene and was used as substrate for allelic exchange by double crossover (FIG. 1A). PCR screening of the hygromycin-resistant transductants with a set of primers (ΔF and ΔR) specific for the deleted segment identified several mutants that failed to amplify the 662-bp expected fragment (data not shown). Disruption of tgs1 by homologous recombination was confirmed by further PCR analysis of the flanking regions (primer pairs E/H1, H2/F) which yielded the expected size products. Southern blot analysis of *M. tuberculosis* wild type and three tgs1 mutants is shown in FIG. 1B. Genomic DNA from *M. tuberculosis* digested with EcoRI and BamHI-EcoRI showed a 5.2 kb and a 2.5 kb hybridization band, respectively when the 5'-flanking region of the construct was used as the probe. DNA from the mutants, under the same conditions showed 1.7 kb band from both digestions, due to the presence of EcoRI site in the hyg gene sequence and absence of BamHI site. RT-PCR analysis showed that the mutant did not produce any tgs1 transcript (FIG. 1C).

The inventors used a replicative shuttle vector, pMIP12 to complement the disrupted mutant by expressing the tgs1 orf under the control of the β-lactamase promoter (pblaF*) of *M. fortuitum*, one of the strongest mycobacterial promoters (18). After electroporation of the expression construct into the tgs1 disrupted mutant, transformants were selected on 7H11 plates supplemented with both kanamycin and hygromycin. Isolated colonies were checked for the restored expression of tgs1. RT-PCR analysis of the complemented strain showed that tgs1 was expressed in it (FIG. 1C).

TG analysis of *M. tuberculosis*, tgs1 mutant and complemented mutant under hypoxia. Previously, the inventors have shown that *M. tuberculosis* accumulates TG under hypoxia, a condition which induces a dormancy-like state in culture (6). To test whether tgs1 deficiency affected the ability to accumulate TG under such conditions, the inventors cultured the cells under hypoxia. The samples from both wild type and tgs1 mutant were collected at 0, 6, 11 and 16 days and extracted lipids were separated by TLC and subjected to dichromate/sulfuric acid charring to visualize TG. tgs1 mutant showed no detectable level of TG at any time points under hypoxic growth condition, whereas wild type started accumulating TG from day 6 and accumulation of TG was maximum at day 16 (FIG. 2A). Lipids were isolated from the silica gel region corresponding to TG and fatty acid analysis was done by GC. This analysis showed that TG from wild type contained all fatty acids ranging from $C_{16}$-$C_{30}$ with $C_{26}$ as the major fatty acid among the longer chain fatty acids, whereas $C_{26}$ fatty acid in tgs1 mutant was virtually absent (FIG. 3). To determine whether TG accumulation could be restored in the tgs1 mutant by providing exogenous fatty acids, the inventors added oleic acid as a BSA complex at days 6, 11 and 16 in both wild type and tgs1 mutant cell cultures. Charring of lipids extracted from these cultures showed that tgs1 mutant at day 11 and 16 contained drastically reduced level of TG when compared to the wild type (FIG. 2B). Even the trace amounts of TG present in the tgs1 mutant contained small amounts of the fatty acids present in the TG in the wild type but $C_{26}$ was absent (data not shown). The small amount of TG produced by the oleic acid supplemented cultures of tgs1 mutant contained oleic acid as a major component and some $C_{16}$ to $C_{24}$ fatty acids in similar proportions as found in the wild type but $C_{26}$ was barely detectable (data not shown).

In a separate set of experiments, the inventors also subjected the complemented strain of tgs1 mutant to the same hypoxic condition to see if the complemented tgs1 strain can restore TG accumulation. Cultures of wild type, tgs1 mutant and complemented tgs1 strain were grown under hypoxia for 16 days and the lipids extracted from the cells were separated by TLC, and the plates were subjected to dichromate/sulphuric acid charring. The results showed that tgs1 mutant was unable to accumulate TG, whereas its complemented strain accumulated TG just as the wild type (FIG. 4). TG isolated from both wild type and complemented strain showed a similar fatty acid profile with $C_{26}$ as the major fatty acid among the longer chain fatty acids, whereas $C_{26}$ fatty acid was virtually absent in tgs1 mutant (FIG. 3).

Acyl chain-length preference and pH optimum of recombinant TGS1. The fatty acid analysis of the TG produced by the wild type and tgs1 mutant suggested that TGS1 may prefer $C_{26}$ fatty acyl-CoA as the substrate. To test for this possibility, the inventors expressed TGS1 in *E. coli* and assayed the TGS activity in the total cell lysate using both $C_{18:1}$- and $C_{26:0}$-CoA as substrates. Results clearly showed that TGS1 has a preference for $C_{26:0}$-CoA over $C_{8:0}$-CoA (FIG. 5A). The $K_m$ values for $C_{26:0}$-CoA and Chd 18:1-CoA were calculated to be 306 μM and 540 μM, respectively from linear double-reciprocal plots. The respective $V_{max}$ values for $C_{26:0}$-CoA and $C_{18:1}$-CoA were calculated to be 2.4 nmol/mg/min and 1.1 nmol/mg/min. The enzyme displayed maximal activity at a wide range of pH from pH 4.5 to pH 7.5 (FIG. 5B).

Role of tgs1 in TG synthesis under acidic and static growth conditions and upon NO treatment. Besides hypoxic stress, dormant bacilli are also believed to encounter other stress factors such as acidic pH in caseous granuloma, slow growth under static phase and NO production inside the host macrophages (4, 9, 20, 25). Therefore, it was tested whether tgs1 mutant is able to accumulate TG under such stress conditions that may share features with the dormant state. *M. tuberculosis* wild type, tgs1 mutant and tgs1-complement strain were grown under acidic stress condition and TG accumulation was analyzed. After three weeks of growth in acidic media the wild type accumulated TG but in tgs1 mutant TG was not detected, whereas its complemented strain accumulated a level of TG similar to that found in the wild type (FIG. 6A). Fatty acid analysis of the TG accumulated under acidic condition showed that the major fatty acids were $C_{16}$-$C_{28}$ with $C_{26}$ as the major component among the longer fatty acids. tgs1 mutant showed no detectable level of $C_{26}$ fatty acid even in the trace amount of TG that was found. Complemented tgs1 mutant showed a TG fatty acid profile identical to that in the wild type (data not shown).

*M. tuberculosis* culture grown under static conditions is known to share features with those of non-replicative latent state (9). To test whether TG accumulates under such a condition and to ascertain whether tgs1 product is involved in TG synthesis under such a condition, it was tested wild type, tgs1 mutant and complemented mutant. Cell cultures grown for two weeks in Middlebrook 7H9 media in a roller incubator, was allowed to settle and were further incubated for 1 week as standing cultures. Total lipids were extracted from these cultures and analyzed by TLC. Dichromate/sulphuric acid charring results showed that tgs1 mutant lost the ability to accumulate TG. The complemented strain accumulated TG to a level similar to the one observed in wild type (FIG. 6B). Fatty acid analysis of the TG from both wild type and complemented mutant strain showed a similar fatty acids profile with $C_{16}$ and $C_{18}$ being the major ones along with very low level of longer chain fatty acids ($C_{20}$-$C_{26}$), whereas in tgs1 mutant that showed the same proportion of smaller chain fatty acids, $C_{26}$ was not even detectable (data not shown).

Treatment of *M. tuberculosis* with NO is known to trigger induction of the hypoxia regulon (21, 30) and cause accumulation of TG (6). To test for the role of tgs1 in TG accumulation, tgs1 mutant and its complemented strain were subjected to NO treatment. After 6 hr of NO treatment, cells were harvested for total lipid extraction. The lipids were separated by TLC, and the dichromate/sulphuric acid charring of the TLC plate showed that the TG level in tgs1 mutant was much less (30%) compared to the wild type, whereas its complemented strain accumulated TG to a level comparable to that found in the wild-type (FIG. 6C). Fatty acid analysis of TG isolated from both wild type and tgs1-complemented strain showed $C_{16}$-$C_{28}$ fatty acids with $C_{26}$ as a major component; however in tgs1 mutant, the level of $C_{26}$ fatty acid was drastically reduced (data not shown).

RT-PCR analyses of tgs transcript levels under various growth conditions. Induction levels of 15 tgs genes were assessed by semiquantitative RT-PCR analyses of mRNA isolated from cells of wild type, tgs1 mutant and tgs1-complemented strains grown under different stress conditions. Transcript levels of tgs genes are expressed as the fraction of 23S rRNA transcript. The tgs1 transcript was completely absent in the tgs1 mutant and it was induced in wild type and tgs1-complemented strains under all the stress conditions, as expected. Transcript levels of other tgs genes under hypoxic, static and acidic growth condition were similar in all the three strains (data not shown). In NO-treated cells of tgs1 mutant transcript levels of Rv3371, Rv1760, Rv2285 and Rv1425 were slightly more than the wild type and tgs1-complemented strain (FIG. 7).

REFERENCES

1. Bardarov, S., S. Bardarov, Jr., M. S. Pavelka, Jr., V. Sambandamurthy, M. Larsen, J. Tufarielo, J. Chan, G. Hatfull, and W. R. Jacobs Jr. 2002. Specialized transduction: an efficient method for generating marked and unmarked targeted gene disruptions in *Mycobacterium tuberculosis, M. bovis* BCG and *M. smegmatis*. Microbiology 148:3007-3017.
2. Betts, J. C., P. T. Lukey, L. C. Robb, R. A. McAdam, and K. Duncan. 2002. Evaluation of a nutrient starvation model of *Mycobacterium tuberculosis* persistence by gene and protein expression profiling. Mol. Microbiol. 43:717-731.
3. Brindley, D. N., S. Matsumura, and K. Bloch. 1969. *Mycobacterium phlei* fatty acid synthase—a bacterial multienzyme complex. Nature 224:666-669.
4. Chan, E. D., J. Chan, and N. W. Schluger. 2001. What is the role of nitric oxide in murine and human host defense against tuberculosis? Current knowledge. Am. J. Respir. Cell Mol. Biol. 25:606-612.
5. Cosma, C. L., D. R. Sherman, and L. Ramakrishnan. 2003. The secret lives of the pathogenic mycobacteria. Annu. Rev. Microbiol. 57:641-676.
6. Daniel, J., C. Deb, V. S. Dubey, T. D. Sirakova, B. Abomoelak, H. R. Morbidoni, and P. E. Kolattukudy. 2004. Induction of a novel class of diacylglycerol acyltransferases and triacylglycerol accumulation in *Mycobacterium tuberculosis* as it goes into a dormancy-like state in culture. J. Bacteriol. 186:5017-5030.
7. Derbyshire, K. M., and S. Bardarov. 2000. DNA transfer in mycobacteria: conjugation and transduction. In G. F. Hatfull and W. R. Jacobs, Jr. (ed.), Molecular genetics of mycobacteria. ASM Press, Washington, D.C. pp. 93-107.
8. Fisher, M. A., B. B. Plikaytis, and T. M. Shinnick. 2002. Microarray analysis of the *Mycobacterium tuberculosis* transcriptional response to the acidic conditions found in phagosomes. J. Bacteriol. 184:4025-4032.
9. Florezyk, M. A., L. A. McCue, A. Purkayastha, E. Currenti, M. J. Wolin, and K. A. McDonough. 2003. A family of acracr-coregulated *Mycobacterium tuberculosis* genes shares a common DNA motif and requires Rv3133c (dosdosR or devdevR) for expression. Infect. Immun. 71:5332-5343.
10. Garton, N. J., H. Christensen, D. E. Minnikin, R. A. Adegbola, and M. R. Barer. 2002. Intracellular lipophilic inclusions of mycobacteria in vitroin vitro and in sputum. Microbiology 148:2951-2958.
11. Gomez, J. E., and J. D. McKinney. 2004. *M. tuberculosis* persistence, latency, and drug tolerance. Tuberculosis (Edinb) 84:29-44.
12. Honer Zu Bentrup, K., A. Miczak, D. L. Swenson, and D. G. Russell. 1999. Characterization of activity and expression of isocitrate lyase in *Mycobacterium avium* and *Mycobacterium tuberculosis*. J Bacteriol. 181: 7161-7167.
13. Jackson, S. K., Stark, J. M., Taylor, S., and Harwood J. L. 1989. Changes in phospholipids fatty acid composition and triacylglycerol content in mouse tissues after infection with bacilli Calmette-Guerin. Br. J. Exp. Path. 70:435-441.
14. Kalscheuer, R, and A. Steinbuchel. 2002. A novel bifunctional wax ester synthase/acyl-CoA:diacylglycerol acyltransferase mediates wax ester and triacylglycerol biosynthesis in *Acinetobacter calcoaceticus* ADP1. J. Biol. Chem. 278:8075-8082.
15. Kikuchi, S., D. L. Rainwater, and P. E. Kolattukudy. 1992. Purification and characterization of an unusually large fatty acid synthase from *Mycobacterium tuberculosis* var. bovis BCG. Arch. Biochem. Biophys. 295: 318-326.
16. Kornberg, H. L., and H. Beevers. 1957. The glyoxylate cycle as a stage in the conversion of fat to carbohydrate in castor beans. Biochim. Biophys. Acta. 26:531-537.
17. Kornberg, H. L., and H. A. Krebs. 1957. Synthesis of cell constituents from C2-units by a modified tricarboxylic acid cycle. Nature 179:988-991.
18. LeDantec, C., N. Winter, B. Gicquel, V. Vincent, and M. Picardeau. 1991. Genomic sequence and transcriptional analysis of a 23-kilobase mycobacterial linear plasmid: evidence for horizontal transfer and identification of plasmid maintence systems. J. Bacteriology. 183: 2157-2164.
19. Munoz-Elias, E. J., and J. D. McKinney. 2005. *Mycobacterium tuberculosis* isocitrate lyases 1 and 2 are jointly required for in vivo growth and virulence. Nat. Med. 11:638-644.
20. Nathan, C. 2002. Inducible nitric oxide synthase in the tuberculous human lung. Am. J. Respir. Crit. Care Med. 166:130-131.
21. Ohno, H., G. Zhu, V. P. Mohan, D. Chu, S. Kohno, W. R. Jacobs, Jr., and J. Chan. 2003. The effects of reactive nitrogen intermediates on gene expression in *Mycobacterium tuberculosis*. Cell. Microbiol. 5:637-648.
22. Park, H. D., K. M. Guinn, M. I. Harrell, R. Liao, M. I. Voskuil, M. Tompa, G. K. Schoolnik, and D. R. Sherman. 2003. Rv3133c/dosR is a transcription factor that mediates the hypoxic response of *Mycobacterium tuberculosis*. Mol. Microbiol. 48:833-843.
23. Russell, D. G. 2003. Phagosomes, fatty acids and tuberculosis. Nat. Cell Biol. 5:776-778.
24. Sassetti, C. M., and E. J. Rubin. 2003. Genetic requirements for mycobacterial survival during infection. Proc. Natl. Acad. Sci. U.S.A. 100:12989-12994.
25. Saviola, B., S. C. Woolwine, and W. R. Bishai. 2003. Isolation of acid-inducible genes of *Mycobacterium tuberculosis* with the use of recombinase-based in vivo expression technology. Infect. Immun. 71:1379-1388.
26. Schnappinger, D., S. Ehrt, M. I. Voskuil, Y. Liu, J. A. Mangan, I. M. Monahan, G. Dolganov, B. Efron, P. D. Butcher, C. Nathan, and G. K. Schoolnik. 2003. Transcriptional adaptation of *Mycobacterium tuberculosis* within macrophages: insights into the phagosomal environment. J. Exp. Med. 198:693-704.
27. Segal, W., and H. Bloch. 1956. Biochemical differentiation of *Mycobacterium tuberculosis* grown in vivo and in vitro. J. Bacteriol. 72:132-141.
28. Sirakova, T. D., A. K Thirumala, V. S. Dubey, H. Sprecher, and P. E. Kolattukudy. 2001. The *Mycobacterium tuberculosis* pks2 gene encodes the synthase for the hepta- and octamethyl-branched fatty acids required for sulfolipid synthesis. J. Biol. Chem. 276:16833-16839.
29. Tufariello, J. M., J. Chan, and J. L. Flynn. 2003. Latent tuberculosis: mechanisms of host and bacillus that contribute to persistent infection. Lancet Infect. Dis. 3:578-590.
30. Voskuil, M. I., D. Schnappinger, K C. Visconti, M. I. Harrell, G. M. Dolganov, D. R. Sherman, and G. K Schoolnik. 2003. Inhibition of respiration by nitric oxide induces a *Mycobacterium tuberculosis* dormancy program. J. Exp. Med. 198:705-713.
31. Wayne, L. G., and K. Y. Lin. 1982. Glyoxylate metabolism and adaptation of *Mycobacterium tuberculosis* to survival under anaerobic conditions. Infect. Immun. 37:1042-1049.
32. Wayne, L. G., and C. D. Sohaskey. 2001. Nonreplicating persistence of *Mycobacterium tuberculosis*. Annu. Rev. Microbiol. 55:139-163.
33. World Health Organization. 2005. Global tuberculosis control. http://www.who.int/tb/publications/2005/en/index.html
34. Zahrt, T. C. 2003. Molecular mechanisms regulating persistent *Mycobacterium tuberculosis* infection. Microbes Infect. 5:159-167.

35. Zhang Y. 2004. Persistent and dormant bacilii and latent tuberculosis. Front. Biosci. 9:1136-1156.

All patents, patent applications, publications, texts and references discussed or cited herein are incorporated by reference to the extent not inconsistent with the teachings herein. In addition, all terms not specifically defined are first taken to have the meaning given through usage in this disclosure, and if no such meaning is inferable, their normal meaning. Where a limitation is described but not given a specific term, a term corresponding to such limitation may be taken from any references, patents, applications, and other documents cited herein.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims. Thus, for the above variations and in other regards, it should be understood that the examples and embodiments described herein are for illustrative purposes only and that various modifications or changes in light thereof will be suggested to persons skilled in the art and are to be included within the spirit and purview of this application and the scope of the appended claims.

Table 1: Set of primers used for making tgs 1 disruption construct in *M. tuberculosis* (SEQ ID NOS 4-17, respectively in order of appearance)

TABLE 1

Set of primers used for making tgs1 disruption construct in *M. tuberculosis* (SEQ ID NOS 4-17, respectively in order of appearance)

| | | |
|---|---|---|
| Primer pairs used to generate 5'- and 3'- flanks of tgs1 genes | | |
| 5' flank | A- | 5'- tcatgatcttggcgatctccagc -3' |
| | B- | 5'- ctgcagggtgattcatggtcagc -3' |
| 3' flank | C- | 5'- ctcgagacgtggtagcagatgcc -3' |
| | D- | 5'- tcatgatacttcccgcactgccc -3' |
| Primer pair inside the deleted segment | | |
| | ΔF- | 5'- ttatcgtcgctc gctcaa cgcc -3' |
| | ΔR- | 5'- tttccgtaatcgcggcaagcgc -3' |
| Primer pair used for genomic flanks | | |
| 5' flank | E,- | 5'- cggcattgatcggtgcccaaccc -3' |
| | H1- | 5'- tgaggcgatggtggtgtcgatgct -3' |
| 3' flank | H2- | 5'- ggaactggcgcagttcctctgggg -3' |
| | F- | 5'- tcacgcccaaactccaacacaccg -3' |
| Primer pair used for RT-PCR | | |
| tgs1 | F- | 5'- tgggtcgtcgacatgggtggcgag -3' |
| | R- | 5'- cgtgctaagtcccgccgcgtc -3' |
| 23S rRNA | F- | 5'- gtggcgtgttctggacccgaagcg -3' |
| | R- | 5'- gtccatcgactacgcctgtcggcc -3' |

What is claimed is:

1. A method of screening for agents potentially useful in the treatment of *Mycobacterium tuberculosis* infection in a mammal comprising the steps of i) contacting a test compound with a *Mycobacterium tuberculosis* triacylglycerol synthase (MTTGS) polypeptide, and ii) detecting binding of said test compound to said MTTGS polypeptide, wherein a test compound which binds to said MTTGS polypeptide is identified as a potential therapeutic agent for decreasing the activity of *Mycobacterium tuberculosis* triacylglycerol synthase.

2. A method of screening for agents potentially useful in the treatment of *Mycobacterium tuberculosis* infection in a mammal comprising the steps of i) determining the activity of a MTTGS polypeptide sequence in the presence of a test compound or in the absence of said test compound, and ii) identifying a test compound that whose presence modulates the activity of said MTTGS polypeptide as a potential therapeutic agent for decreasing the activity of *Mycobacterium tuberculosis* triacylglycerol synthase.

3. A method of screening for agents potentially useful in the treatment of *Mycobacterium tuberculosis* infection in a mammal comprising the steps of i) determining the activity of a MTTGS polypeptide sequence in the presence of a test compound, and ii) determining the activity of said MTTGS polypeptide sequence in the presence of a known regulator of MTTGS, wherein a test compound that modulates the activity of said MTTGS polypeptide sequence to the same extent as said known regulator is identified as a potential therapeutic agent.

4. The method of claim 1, wherein the step of contacting is in or at the surface of a cell which comprises a MTTGS polypeptide.

5. The method of claim 4, wherein the cell is in vitro.

6. The method of claim 1, wherein the step of contacting is in a cell-free system.

7. The method of claim 1, wherein the polypeptide is coupled to a detectable label.

8. The method of claim 1, wherein the compound is coupled to a detectable label.

9. The method of claim 1, wherein a ligand is bound to said polypeptide and the test compound displaces said ligand.

10. The method of claim 1, wherein the polypeptide is attached to a solid support.

11. The method of claim 1, wherein the compound is attached to a solid support.

12. A method of screening for agents potentially useful in the treatment of *Mycobacterium tuberculosis* infection in a mammal comprising the steps of i) contacting a test compound with a *Mycobacterium tuberculosis* triacylglycerol synthase (MTTGS) polynucleotide, and ii) detecting binding of said test compound to said MTTGS polynucleotide, wherein a test compound which binds to said MTTGS polynucleotide is identified as a potential therapeutic agent for decreasing the activity of *Mycobacterium tuberculosis* triacylglycerol synthase.

13. The method of claim 12 wherein the polynucleotide is RNA.

14. The method of claim 12 wherein the contacting step is in or at the surface of a cell which comprises a MTTGS polynucleotide.

15. The method of claim 12 wherein the contacting step is in a cell-free system.

16. The method of claim 12 wherein polynucleotide is coupled to a detectable label.

17. The method of claim 12 wherein the test compound is coupled to a detectable label.

* * * * *

UNITED STATES PATENT AND TRADEMARK OFFICE
CERTIFICATE OF CORRECTION

| | |
|---|---|
| PATENT NO. | : 7,579,012 B2 |
| APPLICATION NO. | : 11/561477 |
| DATED | : August 25, 2009 |
| INVENTOR(S) | : Kolattukudy et al. |

It is certified that error appears in the above-identified patent and that said Letters Patent is hereby corrected as shown below:

In the Specification

Column 1, line 14, please replace the paragraph titled Government Support with the following:

--This invention was made with Government support under agency contract/grant nos. AI046582 and AI035272 awarded by the National Institutes of Health. The Government has certain rights in this invention.--

Signed and Sealed this
Twenty-fourth Day of May, 2016

Michelle K. Lee
*Director of the United States Patent and Trademark Office*